Oct. 13, 1936 J. D. BROWNELL Plant Pat. 200
ROSE
Filed May 9, 1936
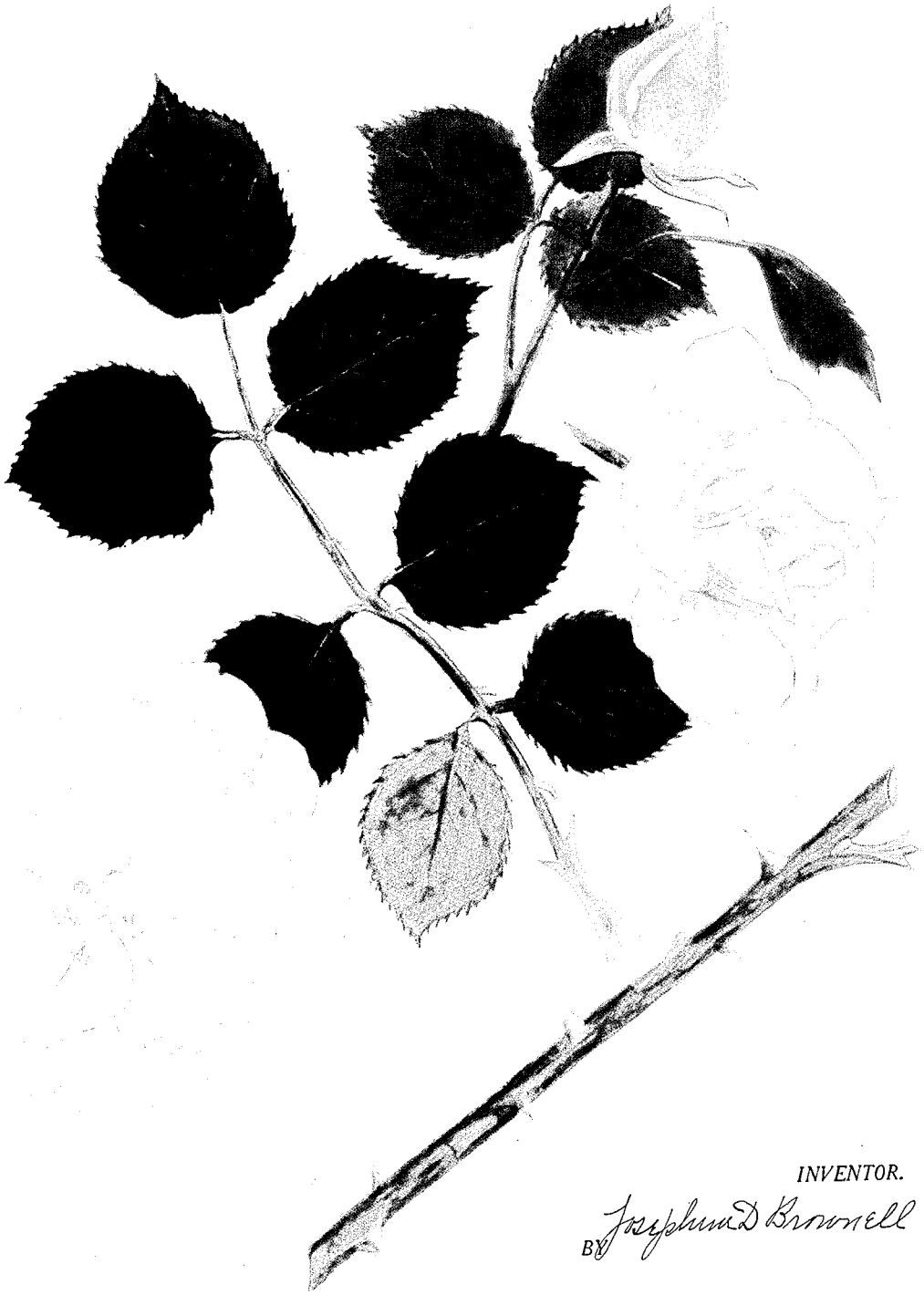
INVENTOR.
BY Josephine D. Brownell
ATTORNEY.

Patented Oct. 13, 1936

Plant Pat. 200

UNITED STATES PATENT OFFICE

200

ROSE

Josephine D. Brownell, Little Compton, R. I.

Application May 9, 1936, Serial No. 78,769

1 Claim. (Cl. 47—61)

My invention relates to roses and especially to a new and original and distinct variety, of the class known commercially as hardy climbing roses and to a subdivision of that class which by virtue of a creeping habit adapts itself also for use as ground cover and embankment decoration which might be designated as trailing or creeping; produced by me in my breeding grounds or research gardens in Little Compton, Rhode Island, and under my directions, by propagating, cross, self and open pollenation, which can be and has been asexually reproduced.

My new rose is new as to the following characteristics and especially as to their joint association in connection with the characteristics of hardiness or immunity from serious injury on account of cold temperatures prevailing in certain parts of the northern portion of the United States;

The unique red to yellow two toned color effect of the petals, being more nearly red and deeper on the outer side and much lighter and more yellow on the inner side;

The nearly imbricated character and variation within certain definite limits of the form of the bloom;

Its character of fragrance and

Its climbing or trailing and branching habit.

In the accompanying drawing forming a part of this specification I have shown my new rose in its natural colors, that is as near as is possible to do so artificially.

I otherwise describe my new rose as follows:

My new rose plant is a hardy hybrid climbing or trailing *Rosa wichuraiana,* crossed in its ancestral geuerations with, in addition to *Rosa wichuraiana* several so called hybrid tea and species roses.

My new rose plant is otherwise described as follows.

*Essential information*

*Type.*—Hardy climbing to nearly decumbent; outdoor; seedling; for cut flowers and garden decoration.

*Class.*—Hybrid climbing wichuraiana; subdivision climbing trailer.

*Breeding or discovery.*—The pollenation which produced my new rose was directed by me and made *July 1, 1930 in my research garden; this seed germinated and was planted in the greenhouse in Little Compton, Rhode Island, in February 1931. The plant therefrom was planted in my said garden in the spring of 1931. This plant can be and has been by me and under my direction asexually reproduced by budding in my said gardens during the months of July in the years 1932 to 1935 inclusive; these propagations reproduced the characters of the original seedlings.

The genealogy of my new rose is to the best of my knowledge and belief as follows: it is a bybrid descendent from the pollen parent known commercially as the climbing Rose Jacotte and the seed parent is a plant being a hardy climbing rose plant produced by the cross between the climbing rose commercially known as Dr. W. Van Fleet as the seed parent and the pollen parent being a yellow rose, identity not definitely known due to the fact that the tag was destroyed by accident prior to picking; it is quite likely that this pollen was from the climbing rose commercially know as Emily Grey.

*Propagation.*—It has held its distinguishing characteristics through succeeding propagations by budding.

*Flower*

*Habit.*—It blooms outdoors in Little Compton, Rhode Island, in late June and July and begins to bloom at about the same time as the climbing rose Dr. W. Van Fleet begins to bloom.

*Flowers borne.*—Singly to fifteen occasionally more; in regular hybrid tea clusters to large open rambler type clusters, usually on strong, woody, stiff and frequently very large stems.

*Quantity of bloom.*—Abundant outdoors in full sunshine, not materially reduced by covering established plant at Little Compton, Rhode Island, with earth for winter protection.

*Continuity.*—One season of three to five weeks according to age and size of plants. No recurrent blooms expected.

*Fragrance.*—Mild, pleasing.

*Bud.*—Size, medium, pointed to slightly ovoid, opens well, being not at all affected by wet or hot weather of reasonable temperature at Little Compton, Rhode Island.

Peduncle, medium in length; medium to heavy, erect to stiff, medium green to frequently slightly bronzy, almost smooth, few reddish hairs.

Foliaceous appendages infrequently extending slightly beyond the tips of the bud.

Color: as calyx breaks and bud begins to open, outer petals outer side nearly (Plate color references, unless otherwise noted are to Ridgway) Grenadine, Plate II, shawing at base to Light Orange-Yellow, Plate III, innerside Pale Orange-Yellow, Plate III, at top shading to Light Orange-Yellow, Plate III, in the middle and Deep Chrome,

*This and other dates herein are approximate.

Plate III, nearer the base and Lemon Chrome, Plate IV, at extreme base. Inner petals of opening bud, outside, Grenadine, Plate II, and Grenadine Red, Plate II, shading on margins to Scarlet, Plate I, inner side Capucine Yellow, Plate III, shading on margins to Flame Scarlet, Plate II, and Bittersweet Orange, Plate II.

*Bloom.*—Is 3 to 4½ inches in diameter when fully open, infrequently more or less; double having petals variable in number, usually varying between 50 and 80. The flower opens high centered, outer and inner petals slightly recurled, intermediate petals frequently more recurled somewhat similar to the ideal hybrid tea type of bloom and suggesting the character of the bloom of its ancestor, Dr. W. Van Fleet, except for the increased petalage, frequently showing pistils and stamens somewhat when fully open.

Petals are in form somewhat variable, outer petals being broadly obovate, concentric rings of petals becoming narrower and slightly shorter toward the center of the flower, to narrowly obovate to cuneate at the base, with some short petals and petaloids, some of which are frequently held, until a mature opening period, attached at both ends; usually one notch at center of terminal edge. Texture medium thick, substantial and leathery, both sides slightly satiny to shiny.

Color of opening flower, outer petals outside Strawberry Pink, Plate I, shading to margins of Peach Red, Plate I, inside upper edge Orange-Pink, Plate II, shading to Apricot Yellow, Plate IV, at base. The tone color of the shadows or lesser lights between opening petals is Rose Doree, Plate I, to Scarlet-Red, Plate I. The color of opening blooms is slightly variable. The foregoing is a substantial average of the colors thereof under favorable conditions.

The color of the open flower grown at Little Compton, Rhode Island, and picked July 3rd, 1935, after four days in the house was, outer petals, outside Hermosa Pink, Plate I, at the terminal and upper border, shading downward to Orange-Pink, Plate II, to Maize Yellow, Plate IV, to Picric Yellow at base, Plate IV; inner side same except Hermosa Pink area was slightly lighter and the Maize Yellow area was larger. These colors of the outer petals gradually in succeeding rows toward the center, shaded to the following colors, of several rows of inner petals, being on the outside upper areas Safrano Pink, Plate II, shading to Picric Yellow at base, inner sides same to slightly lighter.

The flower has a mild delicate tea rose fragance in combination with the fragrance of *Rosa wichuraiana.*

The petals usually drop off cleanly.

*Reproductive organs*

The stamens are variable, frequently in quantity indirectly proportional to the number of petaloids, usually but few of slightly uneven length with light orange to buff anthers.

Filaments medium in length.

Pistils are few, of slightly uneven length.

Styles and stigmas are light greenish yellow.

The ovaries do not protrude from the calyx lobe.

*Plant*

*Foliage.*—Abundant, of compound leaflets, frequently of three leaflets near the flower and five leaflets farther down the stems and frequently seven near the base of the stems and on the canes and branches.

The leaflets are nearly round to oval with prominent, moderately acute apexes with slightly variable rounded bases and frequently one leaflet with the two sides of the base being nonconcentric, causing the base on one side of the midrib to be out of conjunction with that on the other side by a variance of about one sixteenth to one eighth of an inch, as shown in the accompanying drawing with two leaflets on the seven leafleted leaf displayed. The terminal leaflet of seven leafleted leaves is usually slightly larger or wider than the others.

Distinctive characteristics of the leaflets are, thickness and rigidity at maturity, dark color and glossy surface, late seasonal persistence, combining to suggest holly like foliage.

The color of the upper surface at full maturity is slightly darker than Dusky Olive Green, Plate XLI, to Dusky Yellowish Green, Plate XLI, the under side is Pois Green, Plate XLI, shaded with a faint overlay of a misty bluish white with traces of violet near the ribs and margins, (this coloration is pigmentation in the leaflet and not spores attached thereto), edges of young growth tinged reddish, the petioles and rachis are medium slender, frequently before maturity with traces of red and minute hairs on the upper sides or edges and prickles on the under side, frequently four or five, reddish turning lighter at maturity.

The stipules are medium long frequently to one inch, in width usually slightly over ¼ inch with medium points that spread at angles variable usually between 50 and 90 degrees, the edges are slightly hairy. The bush is very vigorous. It is about 10% more vigorous than the climbing variety Dr. W. Van Fleet. Canes are large and normally rigid. The color of the bark is green with reddish shadings and on younger growth it is more light and more reddish. The reddish prickles are somewhat variable in shades turning to dull wood color.

The plant is unusually resistant to black spot and mildew.

*Growth.*—Habit, is repent or creeping as a trailing vine upon the ground, the canes normally lying in a recumbent to decumbent position, substantially in the manner of its ancestor *R. wichuraiana,* being due to the trait of the angle of equilibrium of the canes being nearly 90 degrees in relation to the gravitational influence. It does not normally lie as prostrate as does the species ancestor *R. wichuraiana,* but sufficiently so that it may be grown successfully as a ground cover or embankment decoration, or may be tied up in the usual positions of growing climbing or pillar roses, blooming freely in all such positions.

Canes, medium, prickles several, variable from nearly straight to tips pointing slightly downward.

*Winter resistance.*—From limited tests at Little Compton, Rhode Island, the seedling of this plant has unprotected withstood 23 degrees below zero Fahrenheit to be killed nearly to the ground, to bloom very slightly at the following bloom time, to survive and grow and bloom freely eighteen months after said exposure.

*Comparisons.*—The climbing rose in commerce most closely in comparison with my new rose is Jacotte, which is at Little Compton, Rhode Island, very much less resistant to winter injury, much less vigorous in its early years of growth, requires more time to develop sufficiently to bloom freely, has less than half as many petals and the color shades are very much lighter.

As compared with the climbing rose Mrs. George C. Thomas, this variety also lacks similarly, petalage, depth of color and winter resistance. Neither of these two varieties above compared has the same low angle of equilibrium of my new rose, nor a two toned effect so pronounced as in my rose.

I claim:—

The hardy hybrid *R. wichuraiana* climbing and repent rose plant with hybrid tea to rambler type of bloom cluster as disclosed, characterized by its resistance to moderate subzero temperatures in association with its full petaled semihybrid tea type of bloom, its mild pleasing fragrance, with notably dark holly like foliage, with form and color substantially as shown, being in shades of grenadine red to yellow.

JOSEPHINE D. BROWNELL.